United States Patent
Orszullok

(10) Patent No.: US 9,993,784 B2
(45) Date of Patent: Jun. 12, 2018

(54) DEVICE FOR PREPARING A SOLUTION, IN PARTICULAR IN OR ON A DIALYSIS MACHINE

(71) Applicant: B. BRAUN AVITUM AG, Melsungen (DE)

(72) Inventor: Willy Orszullok, Neuenrade (DE)

(73) Assignee: B. BRAUN AVITUM AG, Melsungen (DE)

( * ) Notice: Subject to any disclaimer, the term of this patent is extended or adjusted under 35 U.S.C. 154(b) by 779 days.

(21) Appl. No.: 14/444,494

(22) Filed: Jul. 28, 2014

(65) Prior Publication Data
US 2015/0029817 A1 Jan. 29, 2015

(30) Foreign Application Priority Data
Jul. 29, 2013 (DE) .................. 10 2013 108 082

(51) Int. Cl.
| | | |
|---|---|---|
| *B01F 15/00* | (2006.01) | |
| *A61M 1/16* | (2006.01) | |
| *B65D 85/804* | (2006.01) | |

(52) U.S. Cl.
CPC ......... *B01F 15/0085* (2013.01); *A61M 1/167* (2014.02); *A61M 1/1666* (2014.02);
(Continued)

(58) Field of Classification Search
CPC .... A61J 1/10; A61J 1/05; A61J 1/1475; A61J 1/1493; A61J 1/2003; B65D 33/02;
(Continued)

(56) References Cited

U.S. PATENT DOCUMENTS

| | | |
|---|---|---|
| 5,616,305 A | 4/1997 | Mathieu |
| 6,308,721 B1 | 10/2001 | Bock et al. |
| | (Continued) | |

FOREIGN PATENT DOCUMENTS

| | | |
|---|---|---|
| CN | 101495163 A | 7/2009 |
| CN | 102946840 A | 2/2013 |
| | (Continued) | |

OTHER PUBLICATIONS

European Search Report for EP 14 17 8790 dated Nov. 20, 2014.
(Continued)

*Primary Examiner* — Tony G Soohoo
*Assistant Examiner* — Elizabeth Insler
(74) *Attorney, Agent, or Firm* — RatnerPrestia

(57) ABSTRACT

Devices for preparing a liquid solution are disclosed. The device includes a receptacle defining a cavity for receiving at least one active substance to be dissolved, at least one inlet leading into the cavity for feeding at least one solvent into the cavity, and at least one outlet leading out of the cavity for discharging the liquid solution including the at least one active substance and the at least one solvent from the cavity. The cavity or the receptacle may include a flexible outer shell for enclosing the cavity and an inner, preferably columnar, supporting element for stretching the flexible outer shell between at least two points, the supporting element comprising the at least one inlet at its first end and the at least one outlet at its second end and being enclosed by the flexible outer shell to provide an axially rigid cartridge that can be used in currently customary dialysis machines comprising cartridge connection systems, which can be produced at low cost.

9 Claims, 7 Drawing Sheets

(52) U.S. Cl.
CPC ....... *A61M 1/1668* (2014.02); *B65D 85/8043* (2013.01); *A61M 2205/7545* (2013.01); *A61M 2206/10* (2013.01); *A61M 2206/20* (2013.01); *A61M 2207/00* (2013.01); *B01F 2215/0034* (2013.01); *B65D 2231/004* (2013.01)

(58) Field of Classification Search
CPC .......... B65D 75/5866; B65D 2231/004; B65D 85/8043; A61M 1/167; A61M 39/10; A61M 1/0001; B01J 8/004
USPC ........................................................ 366/131
See application file for complete search history.

(56) References Cited

U.S. PATENT DOCUMENTS

| | | | |
|---|---|---|---|
| 8,343,129 B2 | 1/2013 | Falkvall et al. | |
| 9,138,380 B2 | 9/2015 | Jansson et al. | |
| 2002/0091371 A1 | 7/2002 | Ritter | |
| 2007/0066955 A1* | 3/2007 | Sparholt | A61M 5/14248 604/415 |
| 2015/0029817 A1 | 1/2015 | Orszullok | |

FOREIGN PATENT DOCUMENTS

| | | | |
|---|---|---|---|
| CN | 204446743 U | 7/2015 | |
| DE | 44 22 100 | 12/1995 | |
| DE | 198 01 107 | 7/1999 | |
| DE | 19801107 A1 * | 7/1999 | .......... A61M 1/1656 |
| DE | 198 52 982 | 3/2000 | |
| DE | 101 00 549 | 7/2002 | |
| DE | 10 2011 017048 | 10/2012 | |
| JP | 2013081538 A | 5/2013 | |
| WO | WO 99/06083 | 2/1999 | |
| WO | WO 2007/144427 | 12/2007 | |
| WO | WO 2011/161064 | 12/2011 | |
| WO | 2012175753 A1 | 12/2012 | |

OTHER PUBLICATIONS

German Search Report for DE 10 2013 108 082.0 dated Mar. 26, 2014.

First Chinese Office Action for Chinese Application No. 201410367102.7, dated May 4, 2017, including English translation, 15 pages.

* cited by examiner

DEVICE FOR PREPARING A SOLUTION, IN PARTICULAR IN OR ON A DIALYSIS MACHINE

CROSS REFERENCE TO RELATED APPLICATIONS

This application claims priority to German application DE 10 2013 108 082.0 filed Jul. 29, 2013, the contents of such application being incorporated by reference herein.

FIELD OF THE INVENTION

The invention relates to a device for preparing a solution, in particular for use in or on an extracorporeal blood treatment machine such as a dialysis machine.

BACKGROUND

In dialysis machines, a dialysis liquid is prepared by dissolving a salt (bicarbonate) stored in a cartridge or by diluting a liquid concentrate with the addition of a liquid stored in a cartridge. The cartridge may be externally clamped in a special cartridge holder of the machine, via which the content of the cartridge is tapped in line with demand. This means that the cartridge holder usually has to fulfill two functions: the supporting of the cartridge as well as tapping the content of the cartridge.

DESCRIPTION OF THE RELATED ART

Cartridge holders for dialysis machines comprising a lower chuck/clamping jaw and an upper chuck/clamping jaw which have integrated connectors for a cartridge, are known in prior art for instance from DE 198 52 982 C1. The employed cartridges are so-called rigid container cartridges which have a sturdy cartridge wall and are produced in particular as PP injection molded part. The cartridges, which in most cases are cylinder-shaped, comprise an intake at an end face and a drain at the opposite end face and are equipped with inserted or molded sieve elements to prevent the escape of any powder or other suspended matter. In such arrangement, the connectors of the cartridge are arranged to be axially opposite and are kept at a fixed distance by the stiff/rigid cartridge body. This allows to connect the cartridge by connectors arranged on the dialysis machine, which are axially pressed onto the connectors (possibly biased by springs). Bag-shaped receptacles cannot be used in the mentioned connector system due to their lack of dimensional stability.

The firm PP injection-molded cartridges are very fragile and often show transport damages. Further, the sieve elements for retaining the powder are separate parts which have to be fastened in a special way. In addition, rigid cartridges tend to implode if their interior is below atmospheric pressure.

With bag-shaped receptacles, however, as they are used in medical science for other purposes (such as for infusion purposes), there is no possibility to connect them to the dialysis machines of the type mentioned above, and complex feed and discharge lines along with sieve elements are required.

SUMMARY OF THE INVENTION

Thus, an object on the basis of the invention is to provide a receptacle which can be used in currently common extracorporeal blood treatment machines such as dialysis machines comprising cartridge connection systems, which eliminates the disadvantages of prior art and can also be produced at low costs.

According to aspects of the invention, a (flexible) bag is equipped with an inner supporting tube element for the device for preparing a solution, the supporting tube element allowing, on the one hand, the connection to the dialysis machine, i.e. it is provided with preferably front-side connectors and, on the other hand, representing at the same time the inflow and outlet element for bag-internal fluids as well as the carrier (stretching means) of the bag. The (flexible) bag may consist of two individual, superimposed foils which are closed by a weld seam extending all around. This weld seam also connects the tube (which extends through the bag produced in this way and projects out of the bag at the top and at the bottom for connection purposes) to the bag in fluid-tight manner (impervious to media). A further embodiment of the bag may be based on a tubular foil.

The generic device for preparing a solution comprises:
a receptacle defining a cavity and intended for receiving at least one active substance to be dissolved,
at least one inlet leading into the cavity and intended for feeding at least one solvent into the cavity and
at least one outlet leading out of the cavity and adapted for discharging the liquid solution consisting of the at least one active substance and the at least one solvent from the cavity.

According to aspects of the invention, the device is further developed in that the receptacle comprises:
a flexible outer shell for enclosing the cavity and
an inner, preferably columnar supporting element for stretching the flexible outer shell between at least two points,
the supporting element comprising the at least one inlet at its first end and the at least one outlet at its second end and being enclosed by the flexible outer shell.

Preferred embodiments of the device according to aspects of the invention comprise one or more of the following features independently or in combination with one another, according to which the flexible outer shell is a tubular foil which has its both openings tightly welded to the supporting element;

the flexible outer shell is formed from a first foil and a second foil which each have their respective edges connected to each other and to the supporting element by a weld seam, so that the supporting element protrudes from the outer shell at the top and at the bottom for connecting purposes;

the supporting element and the outer shell are connected by feed-through flanges;

the supporting element is a tube which comprises a tube closure underneath (downstream of) the at least one inlet and above (upstream of) the at least one outlet;

the supporting element is a tube into which a closure plug is pressed underneath (downstream of) the at least one inlet and above (upstream of) the at least one outlet;

the supporting element is connected/formed in one piece with the at least one inlet and the at least one outlet;

the supporting element comprises at least one sieve element behind (downstream of) the at least one inlet and in front of (upstream of) the at least one outlet, respectively;

the supporting element comprises at least one distribution element equipped with several distribution channels and/or several guide vanes behind (downstream of) the at least one inlet and in front of (upstream of) the at least one outlet, respectively, in order to distribute inflowing solvent in the cavity in a predetermined manner and/or to convey the prepared solution into the outlet in a predetermined manner (preferably uniformly).

Among others, the device according to aspects of the invention has the following advantages:

Due to the fact that the supporting element is surrounded by the container medium in a protective and shock-absorbing manner and the container itself is flexible, the device is extremely break-proof ("not prone to breaking"), so that an increased transport safety is achieved. Due to the flexibility of the container (which does not have to absorb any clamping forces), the device is also vacuum-proof. The device can be produced at low cost. In addition, the device can be connected to common dialysis machines, as the inner supporting element undertakes, among others, the function of the sturdy container wall which is known from prior art.

BRIEF DESCRIPTION OF THE DRAWINGS

The invention is best understood from the following detailed description when read in connection with the accompanying drawings.

DETAILED DESCRIPTION OF THE PREFERRED EMBODIMENTS

Figure 1:
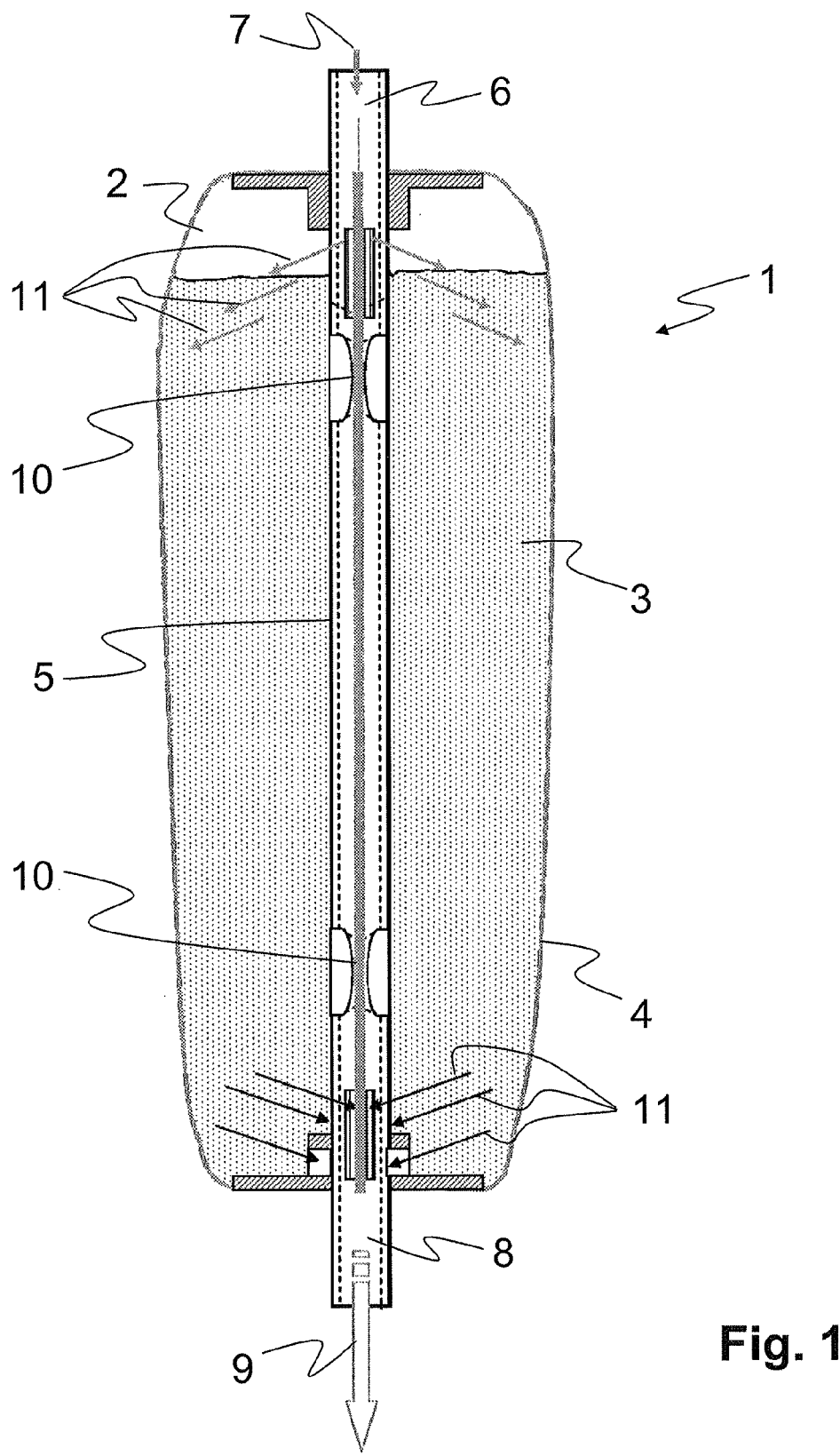
FIG. 1 shows a first preferred embodiment of the device according to aspects of the invention, as seen in cross-section.

FIG. 1 shows a first preferred embodiment of the device according to aspects of the invention comprising a flexible receptacle or bag 1 which surrounds a cavity 2. The cavity 2 is completely or partially filled with an active substance 3 which usually is of granular consistency or exists in powder form. The outer skin of the bag 1 is a flexible outer shell 4 which surrounds the cavity 2 like a balloon or a hose, depending on the volume expansion. The outer shell 4 is supported by an inner (columnar) supporting element 5 which is connected to the flexible outer shell 4 in the vicinity of its first axial end and in the vicinity of its second axial end. The first end of the supporting element 5 extends through the outer shell 4, so that the projecting part of the supporting element 5 serves as an inlet 6 for a solvent 7 into the cavity 2 of the device. The supporting element 5 also has its second end extending through the flexible outer shell 4, so that this projecting part of the supporting element 5 acts as an outlet 8 for the prepared solution 9.

In the illustrated embodiment, the supporting element 5 is substantially designed to be tubular. In order to interrupt the connection between the first end of the supporting element 5 and the second end of the supporting element 5 within the tube body and hence to distribute the solvent 7 in the cavity 2 by necessity, at least one tube closure 10 is provided in the tubular supporting element 5. This ensures that the solvent 7 must travel along predefined solvent paths 11 into the active substance 3 until it reaches the vicinity of the outlet 8 where the solution 9 is collected and transported towards outside via the outlet 8. It is preferred that the tube closure 10 is a hot-stamped tube closure which does not change the static strength of the supporting element (tube) 5. As an alternative, a closure plug can be pressed in.

Inlet 6 and outlet 8 are identical at both axial sides of the container 1 and thus can be installed in any desired way. For the purpose of feeding the liquid via the inlet into the medium inside the container as well as for discharging the solution toward the outlet, distributing and collecting openings are provided in the supporting element 5; the collecting openings for the prepared solution 9 may be arranged in the supporting element 5 slightly above (upstream of) the actual outlet 8 in the form of slits and can be produced by laser cutting processes or fine blanking, for example.

The process of filling the bag 1 according to aspects of the invention with powdery substances is preferably carried out via an opening in the bag at the top (in the region of the inlet 6). For filling purposes, the inner supporting element 5 is pushed aside and the active substance is filled in in dry state. Subsequently, the bag 1 is tightly welded close to the fill opening 23. Alternatively, the opening may be arranged at the top at the side of the inlet 6 and can be sealed by welding or may have a separate closure.

Such a bag-shaped receptacle 1 for powdery active substances (e.g. bicarbonate), which is shown in FIG. 1 and comprises a central supporting and connecting tube, is particularly suited for being used in dialysis machines in which the receptacle 1 is clamped between two fixed intake and drain connections (not shown). The flexible bag 1 along with the axially stable supporting element 5 acting as a central element combines all required functions:

- the possibility of connecting it to dialysis machines of leading manufacturers,
- intake and drain functions for the solvent 7 and the prepared solution 9, respectively,
- the prevention of a direct connection between intake and drain, so that a homogenous mixing is ensured,
- screening function against the escape of powder by corresponding measures which will be explained below,
- connection zones of the supporting element 5 for simplified welding with the bag 1,
- safety against implosion when under negative pressure.

Figure 2:
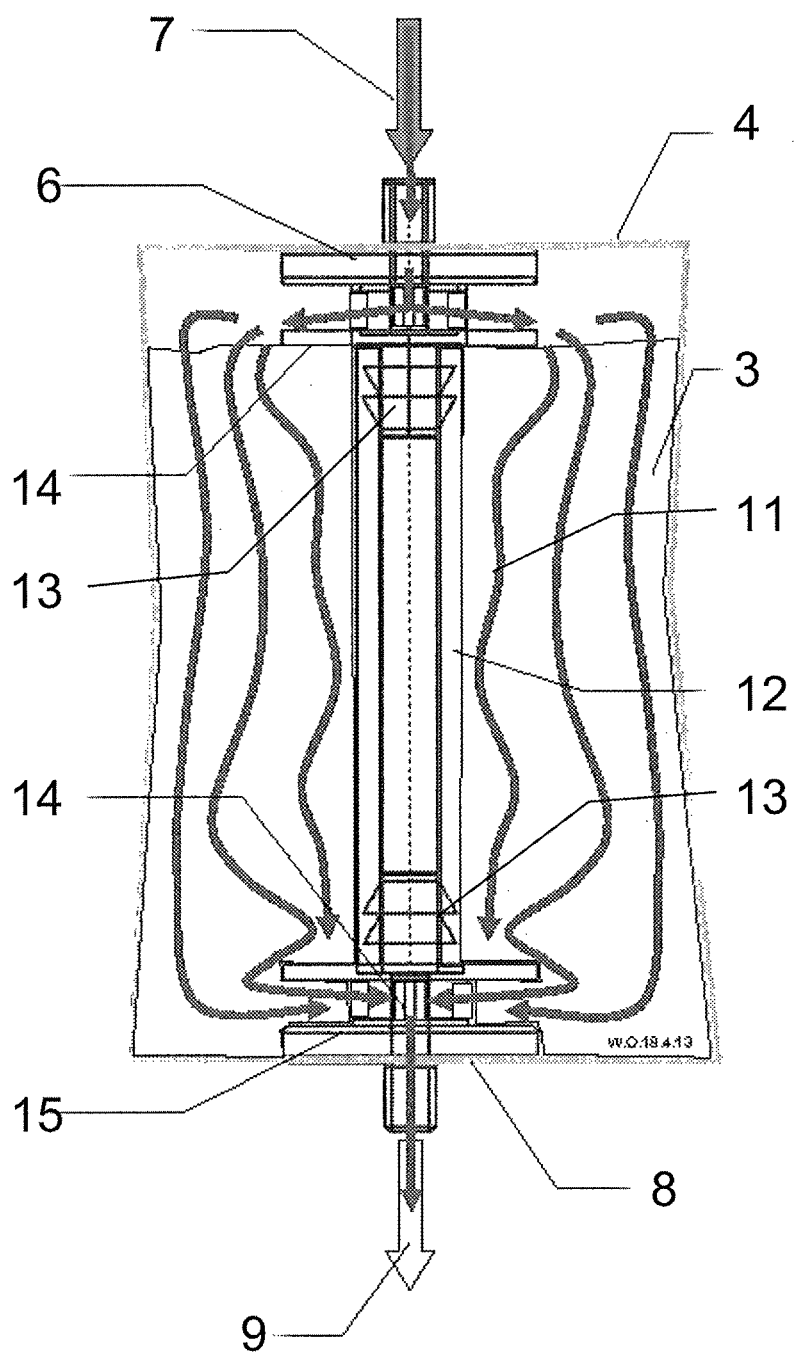
FIG. 2 shows a second preferred embodiment of the device according to aspects of the invention, as seen in cross-section.

FIG. 2 shows a further embodiment of the bag 1 comprising the flexible outer shell 4 which stores the powdery active substance 3. Through an upper carrier- and distribution element which acts as inlet 6 and is arranged on the supporting element, the liquid inflow of the solvent 7 reaches the active substance 3 in a predefined way of distributing or spraying it. In this embodiment, the supporting element 5 is composed of a tube 12 and two end pieces which are connected to the tube 12 by a tube fastening stud 13 in each case. In other words, the intake and drain connectors 6 and 8 are attached to the (carrier- and spacer) tube 12.

The connection pieces 6 and 8, in particular the inflow zone of the inlet 6, are equipped with a disc-shaped distribution plate 14 (flow guiding element) directly behind (downstream of) the distribution/collecting openings in the supporting element 5; said distribution plate prevents the supplied liquid from directly flowing along the carrier tube, in this way preventing the powdery active substance from being washed out in its core around the central axis. At the same time, a good mixing between the liquid and the solid matter is promoted. This is indicated by the solvent paths 11 in FIG. 2.

Further, the connection pieces 6 and 8 may also be provided in particular with gratings or a sieve-like surface, so that granular active substances are retained. This sieve element 15 is situated preferably immediately in front of (upstream of) the outlet 8.

The outer shell 4 of the bag 1 is welded to the carrier element 5 and the connection pieces 6 and 8 in fluid-tight manner. In further embodiments, flange-like discs are provided which are formed on the tube 12 by injection-molding or welding and to which the holed outer shell 4 can be welded/glued. Furthermore, the connection between the supporting element 5 and the bag 1 can be realized by ship-like extensions on the tube 12 which are welded to the outer shell 4.

Figure 3:
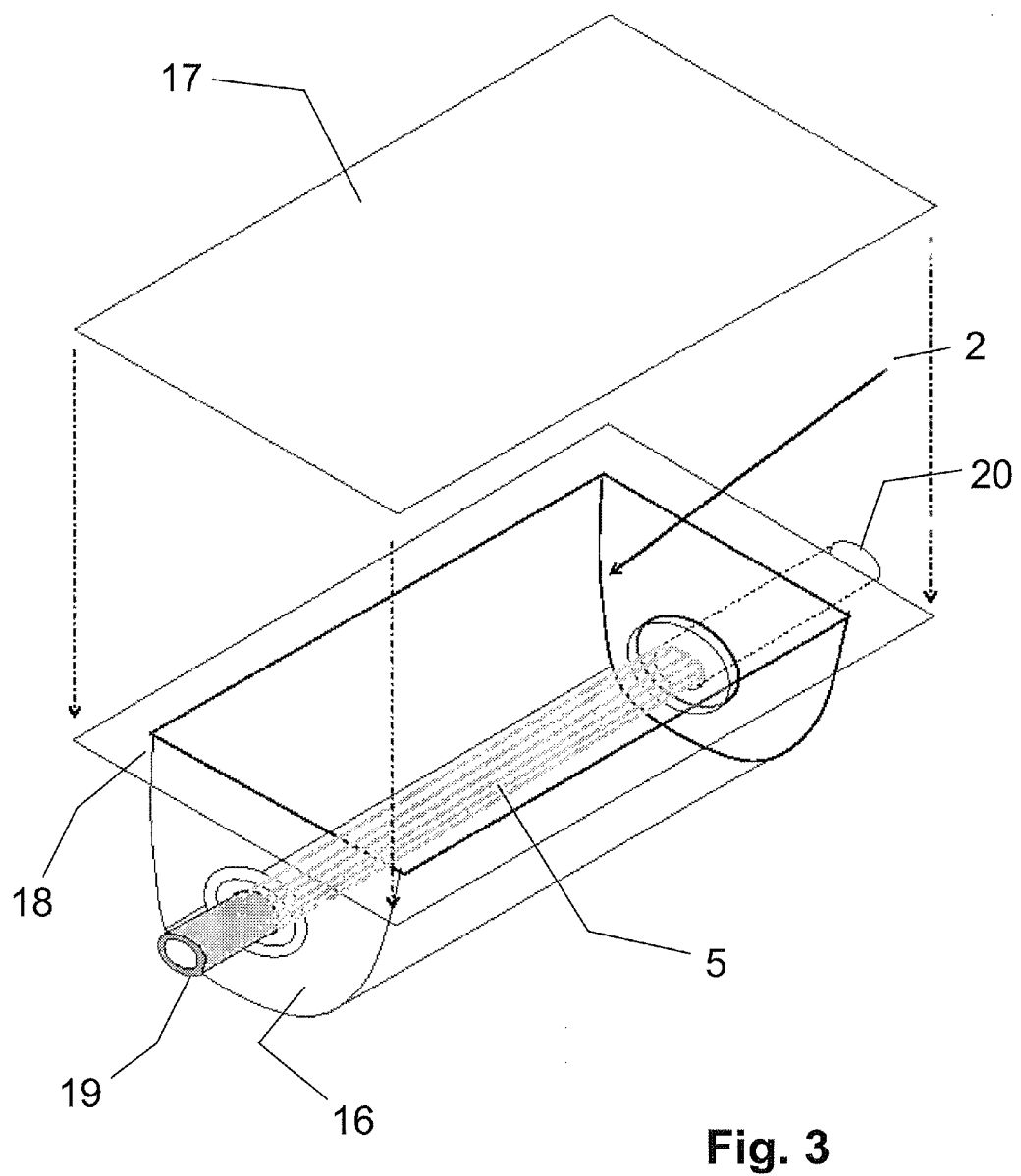
FIG. 3 shows a third preferred embodiment of the device according to aspects of the invention, as seen in cross-section.

In the embodiment according to FIGS. 1 and 2, the outer shell 4 of the bag 1 is illustrated as a one-piece hose. Instead of a hose-like outer shell 4, however, an outer shell 4 composed of two foils may be used for the bag 1. An outer shell of this type is shown in FIG. 3. The outer shell 4 is comprised of a first foil 16 and a second foil 17. In the illustrated embodiment, the first foil 16 has the shape of a trough when it is in the state of maximum expansion. The supporting element 5 extends through the trough and projects toward outside at the two end faces of the trough with its first end 19 and its second end 20 penetrating the first foil 16. Along with the second foil 17, the first foil 16 forms a closed cavity 2. The first foil 16 and the second foil 17 are connected to each other by a weld seam 18.

The embodiment which is shown in FIG. 3 and comprises the trough-shaped first foil 16 offers the advantage of a large fill opening 23 for the active substance which is to be dissolved in the bag 1.

Figure 4:
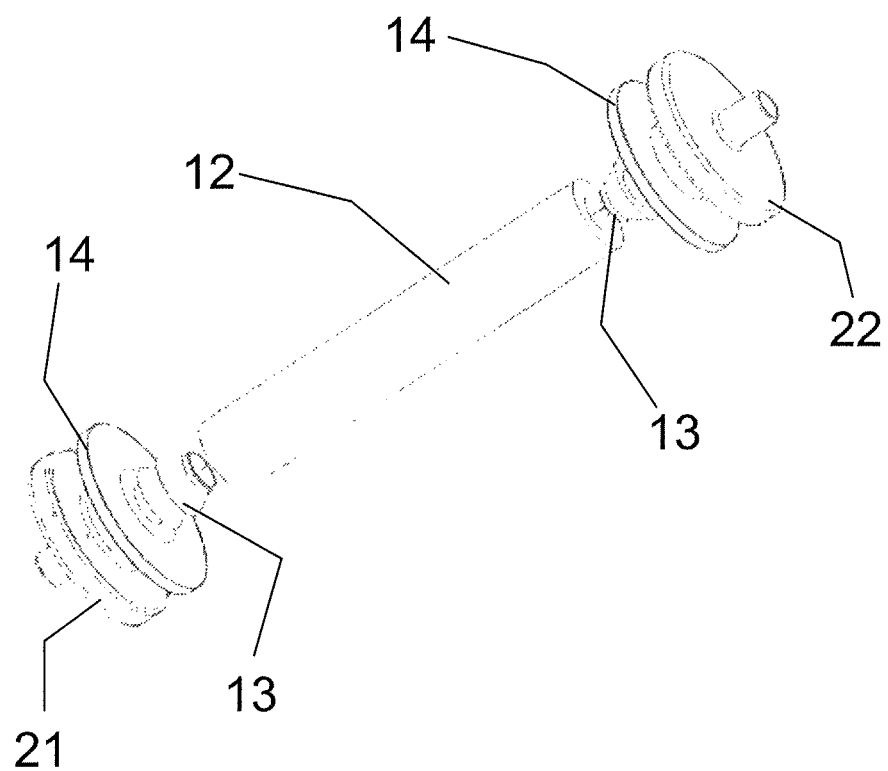
FIG. 4 shows a preferred embodiment of the supporting element according to aspects of the invention, in perspective view.

FIG. 4 shows an embodiment of the supporting element 5 according to aspects of the invention in a perspective illustration. In this embodiment, the supporting element 5 is composed of a tube 12 and a first feed-through flange 21 as well as a second feed-through flange 22. The two feed-through flanges 21, 22 are substantially identical. They are equipped with the required tubular connection to a dialysis machine, which connection serves as an inlet and outlet, respectively, as is shown in FIG. 1. Downstream or upstream of the connection, one or more sieve-like inlet and outlet ports (distributing or collecting openings) are provided. The feed-through flanges 21, 22 may have a round or ship-like design and represent the zone connected to the bag. At the end opposite the connection opening, they are provided with a tube fastening stud (blind plug) 13 in each case. The tube fastening stud 13 is axially pushed (pressed) into a tube socket in the tube 12 (tube interior space) and in this way connected to the tube 12 to form the supporting element 5 according to aspects of the invention. The tube fastening stud 13 is preferably not continuous, so that a tube closure 10 is formed at the same time which prevents the liquid from flowing through the tube 12.

By attaching the feed-through flanges 21, 22 to the respective end of the (e.g. extruded) tube 12, the load-bearing supporting element 5 of the bag 1 is formed. The supporting tube 12 is then connected to the bag 1 by welding.

It is preferred that in particular both of the feed-through flanges 21, 22 are equipped with a plate 14 for the distribution of liquid, as it is also shown in FIG. 2.

Figure 5:
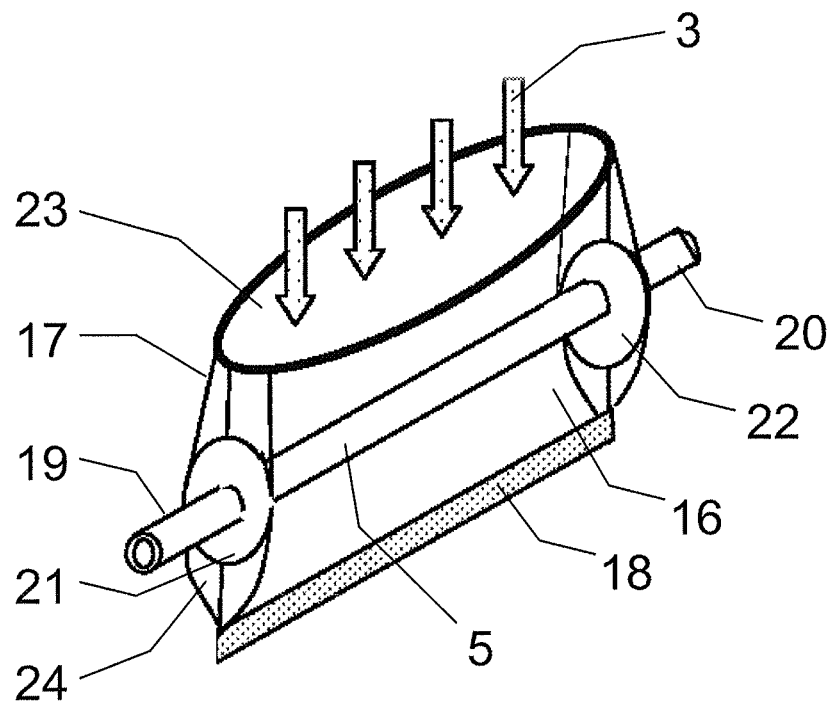
FIG. 5 schematically shows a further preferred embodiment of the device according to aspects of the invention, in perspective view.

The process of filling the bag 1 may also be carried out via an open side seam or partial seam which will be closed after the filling process. This will be explained in the following on the basis of FIG. 5. FIG. 5 shows a bag 1 comprising an outer shell 4 made up of two foils 16 and 17. The foils 16, 17 have their lower sides connected to each other with a weld seam 18. The opposite, upper weld seam is not closed yet, so that there is a fill opening 23 for the active substance 3 to be filled in. This fill opening 23 may be selected depending on the length of the weld seam 18 to have such a width that the filling procedure is easy and, on the other hand, a sufficient strength of the bag 1 is ensured already during the filling process.

At their sides, the two foils 16, 17 are connected to each other with a side part 24 in each case. The side part 24 is a bellows-like foil between the foils 16, 17. Connected to the side parts 24 is the supporting element 5 which penetrates the side parts 24 with its end portions 19 and 20, with the junction between the supporting element 5 and the side parts 24 being sealed by the respective flange 21, 22.

Figure 6:
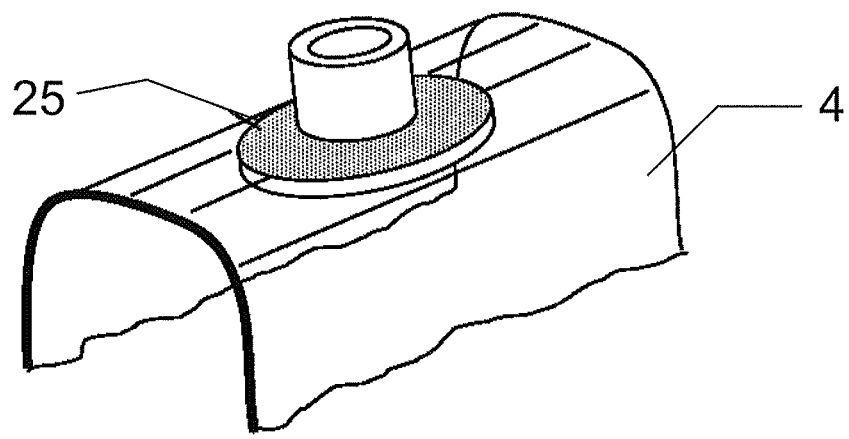
FIG. 6 schematically shows a detail of a further preferred embodiment of the device according to aspects of the invention, in perspective view.

The feed-through point of the supporting element 5 through a foil is not restricted to substantially planar or bellows-like foils. An alternative embodiment is shown in FIG. 6. Due to a stable feed-through flange 25, the supporting element 5 may also penetrate an outer shell 4 which has a more pronounced curvature.

Figure 7:
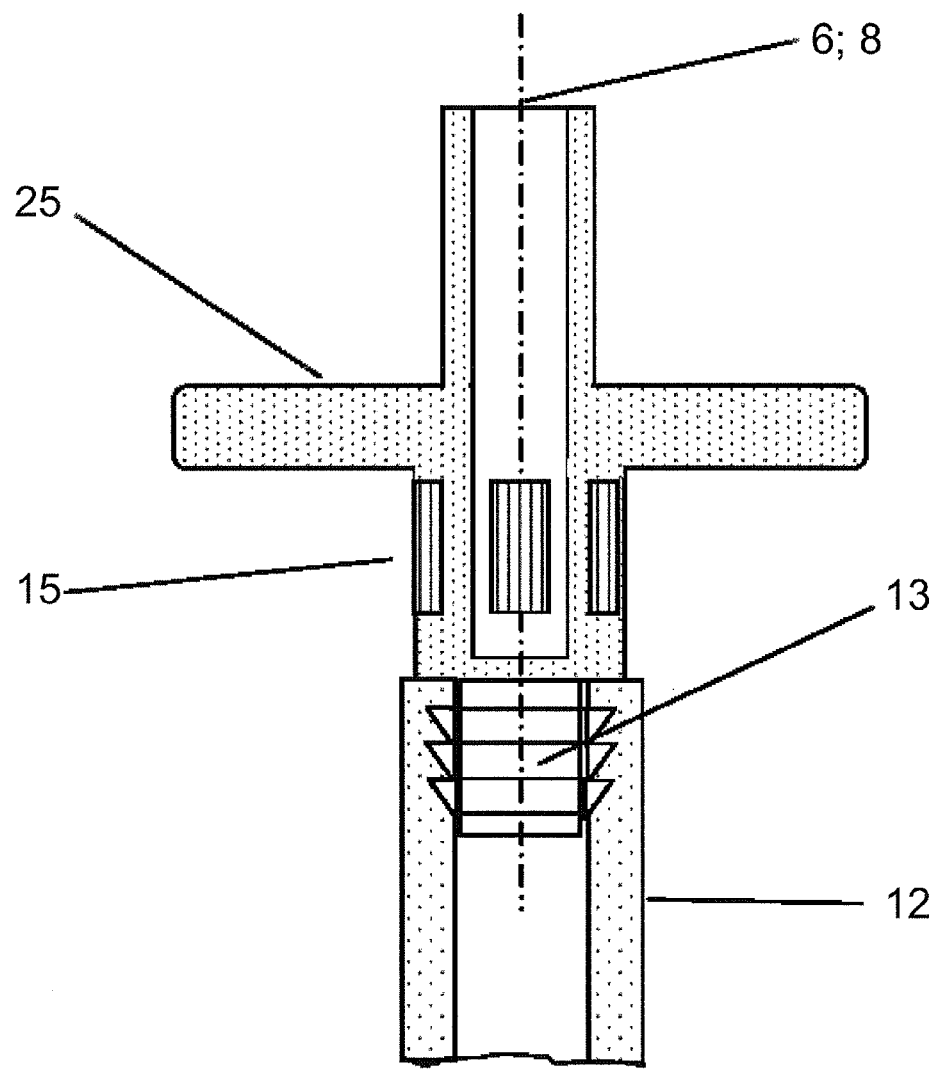
FIG. 7 schematically shows a preferred embodiment of the end of the supporting element according to aspects of the invention, as seen in cross-section.

The structure of the feed-through flange 25 is again shown in FIG. 7. With its integrated liquid channel, the flange 25 serves as inlet 6 and outlet 8, respectively. Via a nozzle 13, the feed-through flange 25 is connected to the tube 12 of the supporting element 5 according to aspects of the invention, the flange 25 preventing any liquid from entering the tube 12. Instead, a sieve element 15 is arranged underneath the flange; the supplied liquid flows through said sieve element into the bag 1 and wets the active substance contained therein. The sieve element 15 may in particular serve as an inflow distributor for the solvent in connection with the liquid distribution plate 14 already described above.

Figure 8:
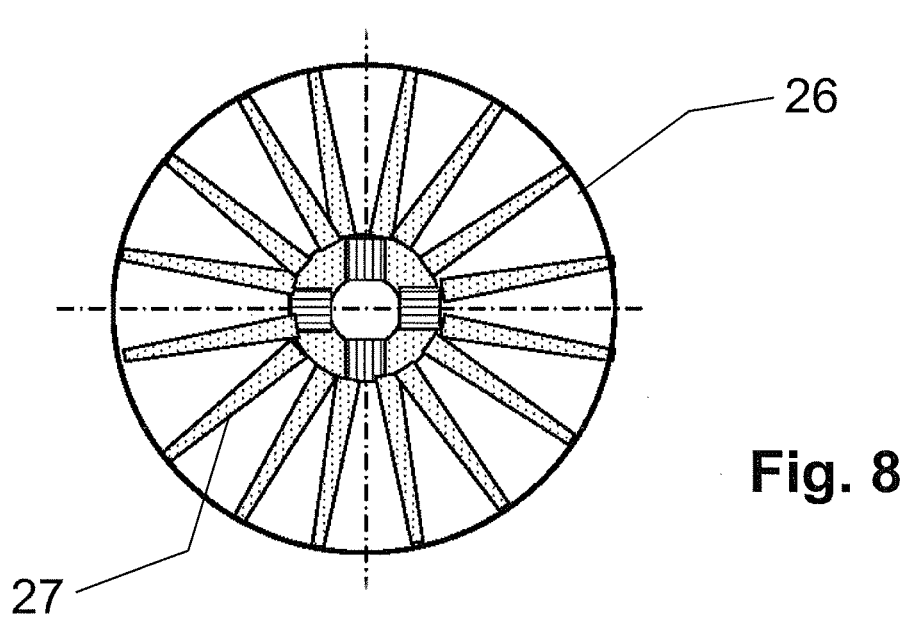
FIGS. 8 and 9 each show a schematic top view of a preferred embodiment of a distribution element which is integrated in the supporting element according to aspects of the invention.
Figure 9:
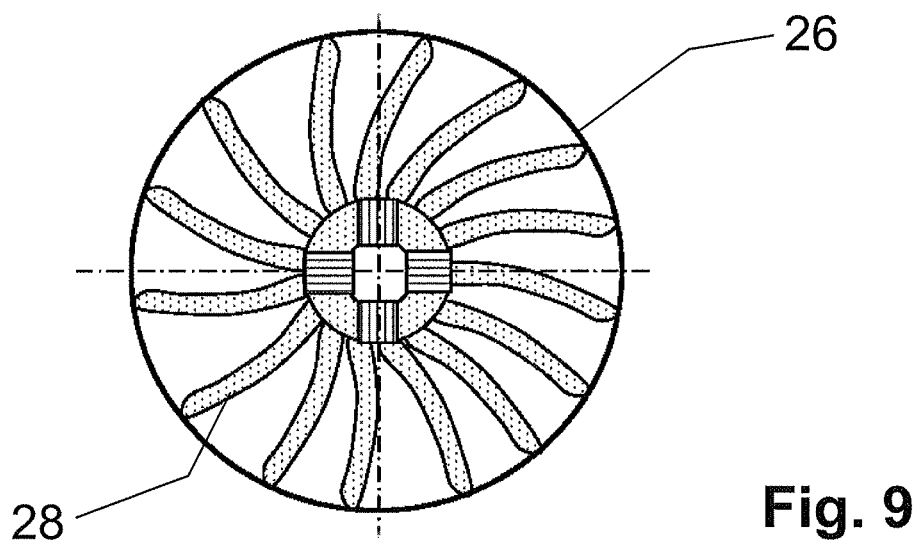

Such a distribution element 26 having a screening function is shown in top view in FIGS. 8 and 9. Here, it is assumed that a distribution plate 14 is formed thereon underneath the liquid inflow as shown in FIGS. 2 and 4. This distribution plate serves for distributing the inflow to a larger surface area of the powder and at the same time prevents a premature wash-out of the powdery active substance along the center line, which might result in a reduced concentration of the solution to be formed. For the purpose of guiding the flow, the distribution element 26 is equipped with distribution channels 27 or guide vanes 28 in straight or also curved shape. This allows to achieve an optimum wetting of the active substance in the bag 1.

The device according to aspects of the invention is not limited to the illustrated embodiments. With respect to the foil container for powdery active substances, in particular a multi-layer or even a mono-foil may be used as the material for the welded bag. A foil made up of the layers PE/PA/PE, which is co-extruded with a total thickness of 200 µm, or a foil made up of the layers PP/PA/PE, which is co-extruded with a total thickness of 150 µm, or a mono-foil made of PP with a layer thickness of up to 900 µm is suitable, for instance. The used wall thicknesses of the foils may be in the range between 150 µm and 900 µm. All mentioned foils may also be used as deep-drawing foils if they have appropriate wall thicknesses. These foils are distinguished by high tear strengths, which is very advantageous in terms of the resistance against negative pressure and the tightness under vacuum of the bag 1 made therefrom, especially in all operational modes where the receptacle is sucked empty with the aid of a negative pressure, as the implosion risk existing with rigid cartridge bodies can be greatly reduced. The above-mentioned materials definitely allow to realize internal pressure loads of the bag of up to 3 bar.

For the purpose of a hygienic sealing and possibly also as an originality closure, a tear-off foil comprising a manipulation tab may be welded to the intake and drain connection pieces after having filled the receptacle 1 with the active substance 3; said foil and/or tab will be removed by pulling them off prior to use. Similarly, attached break-off or twist-off caps which are latched with the container connectors are also conceivable as originality closure.

In summary, the invention relates to a device for preparing a solution, comprising: a receptacle (1) defining a cavity (2) and intended for receiving at least one active substance (3) to be dissolved, at least one inlet (6) leading into the cavity (2) and intended for feeding at least one solvent (7) into the cavity (2), and at least one outlet (8) leading out of the cavity (2) and intended for discharging the liquid solution (9) consisting of the at least one active substance (3) and the at least one solvent (7) from the cavity (2). For providing an axially rigid cartridge which can be used in currently customary dialysis machines comprising cartridge connection systems and can be produced at low costs, it is proposed according to aspects of the invention that the cavity (2) or the receptacle (1) comprises: a flexible outer shell (4) for enclosing the cavity (2), and an inner, preferably columnar supporting element (5) for stretching the flexible outer shell (4) between at least two points, the supporting element (5) comprising the at least one inlet (6) at its first end (19) and the at least one outlet (8) at its second end (20) and being enclosed by the flexible outer shell (4).

The invention claimed is:
1. A device for preparing a liquid solution, comprising:
a receptacle defining a cavity for receiving at least one active substance to be dissolved;
at least one inlet leading into the cavity for feeding at least one solvent into the cavity; and
at least one outlet leading out of the cavity for discharging the liquid solution including the
at least one active substance and the at least one solvent from the cavity;
wherein the receptacle comprises:
a flexible outer shell enclosing the cavity;
an inner supporting element having a first end and a second end for stretching the flexible outer shell between at least two points, the inner supporting element comprising the at least one inlet at the first end and the at least one outlet at the second end and being enclosed by the flexible outer shell, and the inner supporting element being connected to and/or formed with the at least one inlet and the at least one outlet in one piece, wherein the inner supporting element comprises:

a first distribution element having at least one of a plurality of first distribution channels or a plurality of first guide vanes, the first distribution element located downstream of the at least one inlet;
a second distribution element having at least one of a plurality of second distribution channels or a plurality of second guide vanes, the second distribution element located upstream of the at least one outlet; and
a distribution plate located at least one of downstream of the first distribution element or upstream of the second distribution element to at least one of distribute solvent flowing into the cavity or to convey the prepared solution into the outlet; and
wherein the flexible outer shell is formed from a first foil and a separate second foil, which each have their respective edges connected to each other and to the inner supporting element by a weld seam, such that the inner supporting element protrudes for connecting purposes from a top of the outer shell and from a bottom of the outer shell.

2. The device according to claim 1, wherein the flexible outer shell includes two openings tightly welded to the inner supporting element.

3. The device according to claim 1, in which the supporting element and the outer shell are connected by feed-through flanges.

4. The device according to claim 1, wherein the inner supporting element is columnar.

5. The device according to claim 1, in which the supporting element comprises a tube which includes a fluid-tight tube closure underneath the at least one inlet and above the at least one outlet.

6. The device according to claim 1, in which the supporting element comprises a tube which includes a plug underneath the at least one inlet and above the at least one outlet.

7. The device according to claim 1, in which the supporting element comprises a tube into which a closure plug is pressed underneath the at least one inlet and above the at least one outlet.

8. The device according to claim 1, in which the supporting element comprises at least one sieve element behind the at least one inlet and/or in front of the at least one outlet.

9. A device for preparing a liquid solution, comprising:
a receptacle defining a cavity for receiving at least one active substance to be dissolved;
at least one inlet leading into the cavity for feeding at least one solvent into the cavity; and
at least one outlet leading out of the cavity for discharging the liquid solution including the at least one active substance and the at least one solvent from the cavity;
wherein the receptacle comprises:
a flexible outer shell enclosing the cavity; and
an inner supporting element having a first end and a second end for stretching the flexible outer shell between at least two points, the inner supporting element comprising the at least one inlet at the first end and the at least one outlet at the second end and being enclosed by the flexible outer shell, and wherein the inner supporting element comprises:
a first distribution element having at least one of a plurality of first distribution channels or a plurality of first guide vanes, the first distribution element located downstream of the at least one inlet;
a second distribution element having at least one of a plurality of second distribution channels or a plurality of second guide vanes, the second distribution element located upstream of the at least one outlet;
a distribution plate located at least one of downstream of the first distribution element or upstream of the second distribution element to at least one of distribute solvent flowing into the cavity or to convey the prepared solution into the outlet; and
a tube-shaped spacer portion attachably connected to the at least one inlet and the at least one outlet via respective tube fastening studs.

* * * * *